(12) United States Patent
Higgins et al.

(10) Patent No.: US 10,500,535 B2
(45) Date of Patent: *Dec. 10, 2019

(54) SUBMICRON PARTICLE REMOVAL FROM GAS STREAMS

(71) Applicant: Stamicarbon B.V., Sittard (NL)

(72) Inventors: Brian Sayre Higgins, Sittard (NL); John Marshall Tate, III, Sittard (NL); Robert Arthur Yates, Sittard (NL); Marcel Julien Pomerleau, Sittard (NL); Jon Michael Heon, Sittard (NL); Wilfried Marc Renaat Dirkx, Sittard (NL); Juan Coloma González, Sittard (NL)

(73) Assignee: Stamicarbon B.V., Sittard (NL)

(*) Notice: Subject to any disclaimer, the term of this patent is extended or adjusted under 35 U.S.C. 154(b) by 0 days.

This patent is subject to a terminal disclaimer.

(21) Appl. No.: 16/300,434

(22) PCT Filed: May 9, 2017

(86) PCT No.: PCT/NL2017/050287
§ 371 (c)(1),
(2) Date: Nov. 9, 2018

(87) PCT Pub. No.: WO2017/196167
PCT Pub. Date: Nov. 16, 2017

(65) Prior Publication Data
US 2019/0224610 A1    Jul. 25, 2019

(30) Foreign Application Priority Data

May 9, 2016 (EP) ..................... 16168796

(51) Int. Cl.
*B01D 47/06*    (2006.01)
*B01D 47/10*    (2006.01)
(Continued)

(52) U.S. Cl.
CPC ............. *B01D 47/10* (2013.01); *B01D 47/05* (2013.01); *B01D 47/06* (2013.01); *B01D 47/12* (2013.01);
(Continued)

(58) Field of Classification Search
CPC ... Y02P 20/582; B01D 2258/02; B01D 47/06; B01D 47/10; B01D 47/12; B01D 53/40;
(Continued)

(56) References Cited

U.S. PATENT DOCUMENTS 4,104,041 A    8/1978  Arita et al.
4,217,114 A    8/1980  Lagana et al.
(Continued)

FOREIGN PATENT DOCUMENTS

FR    2 519 410    7/1983
GB    1022984      3/1966

OTHER PUBLICATIONS

Boucher, "Etude de quelques nouveaux epurateurs industriels du type venturi", Industrie Chimique, SN, Paris, France (1952) pp. 71-77.
(Continued)

*Primary Examiner* — Timothy C Vanoy
(74) *Attorney, Agent, or Firm* — Morrison & Foerster LLP

(57) ABSTRACT

Disclosed are methods and systems for removing submicron particles from a gas stream, in particular from urea prilling off-gas, wherein a Venturi ejector is used. A method comprises contacting a gas stream containing submicron particles in a Venturi ejector with an injected high velocity scrubbing liquid to provide a pumping action, wherein the scrubbing liquid has an initial velocity of at least 2 m/s and wherein the ratio of scrubbing liquid and gas flow is between 0.0005 and 0.0015 ($m^3/h$)/($m^3/h$). The disclosure also per-
(Continued)

tains to a prilling tower having a gas stream treatment system comprising a Venturi ejector at the top of the prilling tower, and to a method of modifying an existing prilling tower.

19 Claims, 4 Drawing Sheets

(51) Int. Cl.
| | |
|---|---|
| B01D 47/12 | (2006.01) |
| B01D 53/40 | (2006.01) |
| B01D 53/58 | (2006.01) |
| B01D 53/79 | (2006.01) |
| B01J 2/04 | (2006.01) |
| B01D 47/05 | (2006.01) |
| C07C 273/16 | (2006.01) |
| C05C 9/00 | (2006.01) |

(52) U.S. Cl.
CPC .............. *B01D 53/40* (2013.01); *B01D 53/58* (2013.01); *B01D 53/79* (2013.01); *B01J 2/04* (2013.01); *C05C 9/005* (2013.01); *C07C 273/16* (2013.01); *B01D 2247/106* (2013.01); *B01D 2251/206* (2013.01); *B01D 2251/2067* (2013.01); *B01D 2251/304* (2013.01); *B01D 2251/402* (2013.01); *B01D 2251/404* (2013.01); *B01D 2251/50* (2013.01); *B01D 2251/502* (2013.01); *B01D 2251/504* (2013.01); *B01D 2251/506* (2013.01); *B01D 2251/602* (2013.01); *B01D 2251/604* (2013.01); *B01D 2251/606* (2013.01); *B01D 2251/70* (2013.01); *B01D 2258/02* (2013.01); *Y02P 20/582* (2015.11)

(58) Field of Classification Search
CPC .. B01D 53/58; B01D 53/79; B01D 2247/106; B01D 2251/206; B01D 2251/2067; C07C 273/16; C07C 273/00; C07C 273/02; B01J 2/04; C05C 9/005
See application file for complete search history.

(56) References Cited

U.S. PATENT DOCUMENTS

| | | | |
|---|---|---|---|
| 4,424,072 | A | 1/1984 | Lerner |
| 4,507,129 | A | 3/1985 | Storen |
| 4,690,245 | A | 9/1987 | Gregorich et al. |
| 8,753,567 | B1 | 6/2014 | Davis, Jr. |

OTHER PUBLICATIONS

Gamisans et al., "Gas pollutants removal in a single- and two-stage ejector-venturi scrubber", Journal of Hazardous Materials (2002) B90:251-266.
Harris, "Fume scrubbing with the ejector venturi system", Chemical Engineering Progress (1966) 62(4):55-59.
International Preliminary Report on Patentability for PCT/NL2017/050287, dated Sep. 19, 2018, 9 pages.
International Search Report for PCT/NL2017/050287, dated Oct. 4, 2017, 4 pages.

SUBMICRON PARTICLE REMOVAL FROM GAS STREAMS

CROSS-REFERENCE TO RELATED APPLICATIONS

This application is the national phase of PCT application PCT/NL2017/050287 having an international filing date of 9 May 2017, which claims benefit of European patent application No. 16168796.7 filed 9 May 2016. The contents of the above patent applications are incorporated by reference herein in their entirety.

FIELD OF THE INVENTION

The invention pertains to removal of particles from a gas stream, in particular to removing submicron urea dust from a gas stream from a urea prilling tower.

BACKGROUND

Removal of submicron particles from gas streams is often critical for ensuring compliance with emission limits for many industrial processes, such as urea finishing. For instance off-gas from urea prilling towers contains a relatively large amount and/or large fraction of submicron particles, for instance compared to the off-gas from a urea fluid bed granulator. Hence, the removal of submicron urea particles is particularly important in order to meet ever more stringent regulations and limits on the emission of urea. The removal of ammonia from urea finishing off-gas is also necessary. Background references relating to the removal of urea dust from off-gas from a urea finishing section include WO 2015/002535 and WO 2015/072854.

It may be observed that particle size distribution of urea prilling tower off-gas has a peak between 0.1 μm and 1 μm aerodynamic particle size, with a cumulative mass of for example about 70 mg/Nm$^3$ provided by particles <10 μm (about 50 wt. % total particulate matter, PM). Off-gas from urea granulation may for example contain about 25 mg/Nm$^3$ of particles <10 μm. For compliance with current and future emission limits, significant removal of submicron particles, e.g. urea dust, is essential. Available particle capture technologies generally have very low efficiency for submicron particles or have a large pressure drop.

In urea prilling, urea melt is supplied at the top of a prilling tower, and distributed as droplets. The urea melt droplets solidify as they fall down while cooling against a large quantity of upward-moving air. Urea prills are withdrawn from the bottom. The fresh cooling air enters the bottom of the prilling tower. The off-gas comprising urea and ammonia leaves the prilling tower near the top.

A prilling tower can for instance have a height of for example 60 m to 80 m. Smaller plants may have a free fall path of 50 m or less. Some of the largest plants have prilling towers of 125 m height. Emissions can for example be 0.5 to 2.5 kg urea dust per ton urea prills (35 to 125 mg/Nm$^3$) and about 0.5 to 2.7 kg NH$_3$ per ton (35-245 mg/Nm$^3$). Urea dust emissions of more than 200 mg/Nm$^3$ have been reported for some existing urea prilling towers. An example indicative air flow for a urea prilling tower is 500 000 Nm$^3$/hr. A larger urea prilling tower may for instance have 900 000 Nm$^3$/hr, with a urea capacity of 75-100 mt/hr (metric ton per hour).

Older prilling towers frequently vent off-gas directly to air without any urea or ammonia abatement. The tower construction generally sets a maximum for the weight for the design of any abatement systems installed on top as part of revamping. The off-gas from some prilling towers has a low pressure drop, in particular the off-gas from prilling towers operating with natural draft. Existing emission abatement technologies typically would require large blowers and fans to maintain sufficient pressure drop, since generally submicron particle removal requires high pressure drop. Current systems are hence not suitable for installation on top of an existing prilling tower. The possibility of first bringing the off-gas to lower elevation through a duct would introduce an additional significant pressure drop. In view of the large airflows this would lead to a significant increase of the power consumption. The construction of a duct from the top to the bottom of the urea prilling tower is also challenging and expensive, and introduces the risk of plugging in the duct between the prilling tower and the emission abatement system.

For currently available emission abatement technologies, dust scrubbers, especially if combined with an acid washer to reduce ammonia emissions, are generally considered to be feasible only for forced draft prilling towers where air fans are available, and not for natural draft urea prilling towers. For instance U.S. Pat. No. 4,424,072 to Lerner shows in FIG. 1 an apparatus comprising vertical urea prilling tower 11 with a plurality of scrubbers 17 provided above the top of the tower. This patent teaches that the apparatus includes facilities for injecting a stream of air into the lower part of the prilling tower, accomplished by forced draft, induced draft, or combination thereof. As used in the art, induced draft towers use a centrally located fan at the top and forced draft cooling towers use a fan located near the bottom.

Accordingly, there is a need for more effective emission abatement systems and methods that can operate with a low pressure drop and can effectively remove submicron particles from gas streams. More in particular, there is a need for better urea and ammonia emission abatement systems and methods for urea prilling towers.

SUMMARY OF THE INVENTION

In order to better address one or more of the above mentioned desires, the invention pertains, in one of the aspects, to a method for removing submicron particles from a gas stream, the method comprising: contacting a gas stream containing submicron particles in a Venturi ejector with an injected high velocity scrubbing liquid to provide a pumping action, wherein the scrubbing liquid has an initial velocity of at least 25 m/s and/or wherein the ratio of scrubbing liquid and gas flow is between 0.0005 and 0.0015 (m$^3$/h)/(m$^3$/h).

The invention also pertains, in a further aspect, to a gas treatment system comprising a Venturi ejector. The invention also pertains, in yet a further aspect, to a urea prilling tower, in particular a natural draft urea prilling tower, having two Venturi ejector stages at the top.

A further aspect pertains to a method of modifying existing plants, in particular urea prilling towers, comprising addition of a Venturi ejector.

The invention also pertains to a gas stream treatment method comprising subsequently: A) providing a gas stream, B) spraying an aqueous solution into the gas stream, C) passing the gas stream through a first ejector Venturi scrubber having a throat, wherein an aqueous scrubbing liquid is sprayed into the gas stream in the direction of the throat, D) spraying an aqueous solution into the gas stream, F) passing the gas stream through a second ejector Venturi scrubber having a throat, wherein an aqueous scrubbing liquid is sprayed into the gas stream in the direction of the throat; preferably using in step C and/or step F a Venturi ejector with scrubbing liquid having a velocity and/or ratio as described.

DETAILED DESCRIPTION

Figure 1:
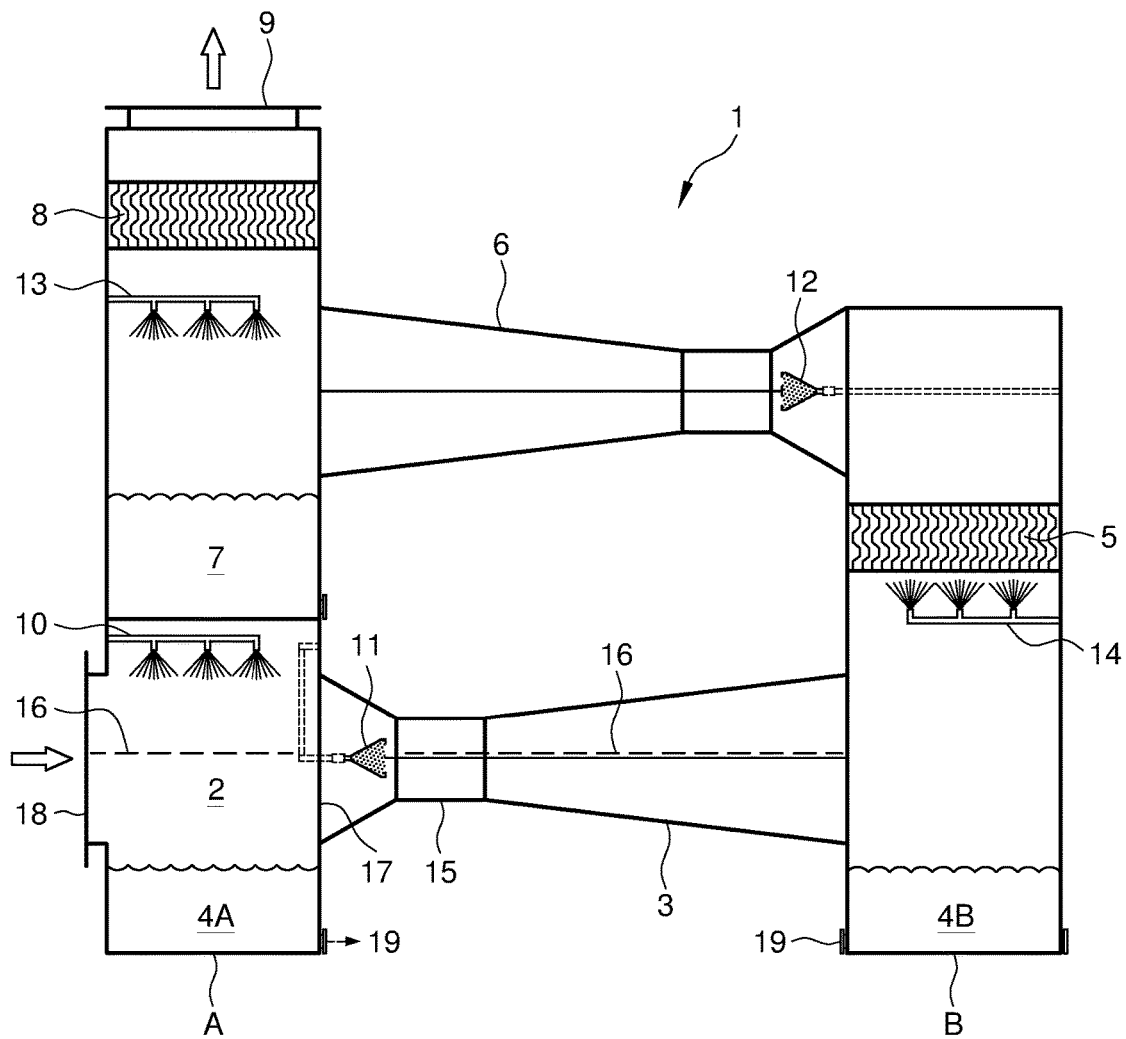
FIG. 1 depicts a block diagram of an embodiment of a system of the invention.

The present invention provides in an aspect a method for removing submicron particles from a gas stream comprises contacting the gas stream containing submicron particles in a Venturi ejector with a scrubbing liquid. The scrubbing liquid is preferably injected, and preferably injected with high velocity, in particular to provide a pumping action. In this way the gas stream to be treated is drawn into the Venturi ejector. The scrubbing liquid preferably has an initial velocity of at least 25 m/s, more preferably at least 50 m/s, even more preferably at least 100 m/s. Such velocities refer for example to the velocities at a nozzle opening and/or to the mean droplet velocity over e.g. 1 cm from the nozzle. Preferably, the method comprises injecting scrubbing liquid in a Venturi ejector with a hydraulic nozzle, such as a high pressure hydraulic nozzle, e.g. with a nozzle pressure of at least 15 bar or at least 18 bar, or with a dual fluid (gas and liquid) nozzle, which may have a pressure lower than 15 bar, in order to provide such preferred velocities.

Preferably, scrubbing liquid is injected in a Venturi ejector so as to give a mean droplet diameter of less than 300 μm, more preferably less than 200 μm. In some embodiments, the method comprises injecting scrubbing liquid in a Venturi ejector through a nozzle configured to provide droplets with a mean droplet diameter of less than 300 μm, preferably less than 200 μm. Droplet sizes are e.g. Volume Median Diameter. This droplet size may contribute to efficient scrubbing. Scrubbing liquid droplets of this size can for example be provided by using the mentioned scrubbing liquid velocities. In particular a hydraulic nozzle with an injection pressure of at least 15 bar can be used, more preferably at least 18 bar or a dual fluid injector which uses compressed gases, of e.g. 3 to 6 bar, to finely atomize the scrubbing liquid, of e.g. 3 to 6 bar.

Preferably, the ratio of scrubbing liquid and gas flow is between 0.0005 and 0.0015 (m$^3$/h)/(m$^3$/h) in at least one Venturi ejector or in each Venturi ejector stage. An example ratio is a ratio of scrubbing liquid to gas flow of 0.00010 to 0.0050 (m$^3$/h)/(m$^3$/h), although lower or higher ratios are also possible. The ratio is for example based on actual m$^3$ of the gas stream to be drawn into the Venturi ejector. Optionally, the scrubbing liquid/gas ratio is in the range of 0.5 to 1.5 l/m$^3$, based on actual m$^3$. Using such ratio, preferably in combination with a scrubbing liquid initial velocity as described, advantageously provides for a surprisingly good scrubbing efficiency in particular with relatively small equipment size and a small pressure drop.

Preferably, the method comprises using a plurality of Venturi ejectors in series. Preferably, the residence time of the gas stream between the first and the downstream second Venturi ejector is at least 0.1 s, or at least 0.20 s, more preferably, at least 0.4 s, for example more than 0.8 s. This relates to the residence time between two Venturi ejectors without other Venturi ejectors between them. Other elements may be present between them, such as a sprayer or a mist eliminator. Using such a residence time between two consecutive Venturi ejectors in series contributes to particle growth, especially of submicron particles. This improves particle capture in for example a downstream particle removal device such as a mist eliminator.

Preferably, a first upstream and a second downstream Venturi stage are used each comprising one Venturi ejector or a plurality of parallel Venturi ejectors. Preferably, the first scrubbing liquid of the first Venturi stage comprises at least 10 wt. % or at least 20 wt. % or at least 30 wt. % or at least 40 wt. % dissolved material, such as 20 to 55 wt. % or 40 to 50 wt. %, and/or such amounts of hydrophilic material, or such amounts of material of components removed from the gas stream. Preferably, the dissolved material is urea and the scrubbing liquid comprises such amount of urea. In some embodiments, the first scrubbing liquid comprises less than 90 wt. % water, or less than 80 wt. %, or even less than 60 wt. %. The scrubbing liquid used in the second downstream Venturi stage and/or in a spray nozzle downstream of the first Venturi stage preferably comprises 0 wt. % to 5.0 wt. % dissolved material, more preferably less than 2.0 wt. % dissolved material, in particular for urea. Preferably, the second scrubbing liquid comprises 80 wt. % to 100 wt. % water, or at least 90 wt. %, or at least 95 wt. % water. Preferably, the scrubbing liquid used in the first Venturi ejector stage (first scrubbing liquid) has a higher concentration of dissolved material than the scrubbing liquid used in the second Venturi ejector stage (second scrubbing liquid), preferably at least 3 times higher or at least 5 times higher or more preferably at least 10 times higher. The scrubbing liquid used in the first Venturi stage, in particular in the most upstream Venturi ejector, is for example the first point of contact with the off-gas.

The first scrubbing liquid is generally recirculated to provide such concentrations of dissolved material (e.g. urea) so as to allow for easier disposal, in particular urea recovery. In particular in case of off-gas (cooling air flow) from prilling or granulation, the prilled or granulated material is preferably recovered. This applies in particular to urea granulation or prilling. The recovered urea may be incorporated in a urea-containing product, e.g. the prills or granules. Generally, a stream comprising such concentrations of urea, e.g. 40 wt. % to 50 wt. % is withdrawn from the first Venturi stage and/or an upstream quench stage as purge and/or blowdown stream, in particular from the collection basin or recirculation loop of these. Hence, the bulk of the particulate material in the gas stream is for example captured by scrubbing with scrubbing liquid comprising such high concentrations of dissolved material.

Introducing a liquid having a lower dissolved material concentration (e.g. urea concentration) than used in a first Venturi stage in the gas stream downstream of the first Venturi ejector may result in an increase of the partial water vapor pressure in the gas stream. This may promote condensation of water on submicron particles, resulting in an increase of the particle size. This can improve capture of the now larger particles in a downstream particle and/or droplet capture device, such as for example (a part of) a Venturi ejector (e.g. a diverging tube part) and/or mist eliminator. In particular condensation on submicron particles and/or aerosol droplets containing urea in relatively higher concentration, such as at least 50 wt. %, or even 100% urea, can be promoted. In some embodiments, the method comprises evaporating at least 0.001 kg/Nm$^3$ or at least 0.005 kg/Nm$^3$ or at least 0.010 kg/Nm$^3$ water downstream of a first Venturi ejector stage and upstream of the throat of a Venturi ejector and/or droplet removal device.

Preferably, the gas stream is obtained from a urea finishing section, such as a urea granulator or a urea prilling tower, more preferably a urea prilling tower. The urea prilling tower is for example a forced draft or a natural draft urea prilling tower.

The present method and system are especially advantageous for use with natural draft urea prilling towers. Natural draft urea prilling towers are urea prilling towers which do not use a fan and/or blower to move the cooling air through the prilling zone of the urea prilling tower. Typically such towers do not use fans or blowers to move cooling air through the urea prilling tower. Typically urea prilling towers are of the forced draft type (fans at bottom), induced draft type (fans at the top), or natural draft type. A natural draft urea prilling tower may still use an ejector e.g. in the off-gas treatment system.

Optionally, the process further comprises a step of urea prilling or urea granulation. Optionally, the process comprises solidification of a urea melt to produce urea prills or granules, using air for cooling of the urea melt droplets.

In some embodiments, the gas stream contains a concentration of submicron particles greater than 20 mg/Nm$^3$, or greater than 50 mg/Nm$^3$, more preferably such concentration of urea particles. Submicron particles have a particle size of 1.0 µm or less. Optionally, the percentage of submicron particles is at least 0.5 wt. % and/or at most 5.0 wt. % of the total weight of the particles in the gas stream, preferably of particles smaller than 1.0 µm, and optionally the amount of such particles is in the range 1.0 to 4.0 wt. %.

Preferably, the submicron particles are hydrophilic. Preferably, the submicron particles comprise a hygroscopic material. Preferably, the submicron particles are dissolvable in the scrubbing liquid, e.g. in water. As used herein, submicron particles encompass for example colloidal aerosols. Condensation may optionally involve condensation onto a particle, droplet, or colloidal aerosol, causing it to grow in size.

The Venturi ejector as used herein is a type of Venturi scrubber and generally comprises, consecutively in series in the direction of the gas flow, a converging tube part, a throat, and a diverging tube part, wherein the converging and diverging part are usually conical tube parts. The throat usually provides a narrow opening for passage of the gas stream and liquid supplied into the gas stream upstream of the throat. The throat may be provided for example by a joint between two parts, e.g. tube parts, or for example by a tube internal cross-section minimum. The acceleration and/or high velocity in the throat and/or converging part contributes to intimate mixing of the gas and liquid, and to turbulence and atomization of the liquid. At least some particles in the gas stream impact on droplets and are entrained and may be removed in a downstream droplet removal device.

Preferably, the Venturi ejector (e.g. ejector Venturi scrubber) comprises a nozzle positioned for spraying scrubbing liquid in a direction parallel with the gas flow (of the gas stream to be treated) through the gas inlet of the Venturi ejector. Optionally, the centerline of the nozzle is parallel to the gas flow. Preferably, the nozzle is inserted into a converging part, such as a conical tube part, of a Venturi ejector.

In some embodiments, the nozzle is spaced apart from a wall of a Venturi tube or duct part. Preferably, the gas inlet of the Venturi ejector is an opening extending substantially perpendicular (e.g. at an angle between 60° and 120° or between 85° and 95°) to the line from the nozzle to the throat of the Venturi. Preferably, the gas inlet of the Venturi ejector is arranged substantially parallel to the opening of the throat. Preferably, the gas flow centerline of the gas to be treated does not bend between nozzle and throat (irrespective of converging of the flow). Preferably, the nozzle is positioned for spraying perpendicular to the throat cross-section and preferably the nozzle is centered to the throat cross section. Generally, the nozzle is spaced and upstream from the throat cross section. In some embodiments, liquid is supplied into a round throat Venturi ejector only through one such nozzle.

The nozzle used to introduce the scrubbing liquid in a Venturi ejector is for instance hydraulic, producing small droplets through high pressure, or for example a dual fluid nozzle, wherein a liquid and an auxiliary gas stream, typically at pressure, flow both through the nozzle. Small droplets can be produced through shear forces between the liquid and gas that both travel through the nozzle.

The scrubbing liquid spray acts as motive fluid for the Venturi ejector, together with the air stream in case of a dual fluid nozzle. Hence, the Venturi ejector may acts as Venturi eductor wherein the gas stream to be treated is drawn in with the motive fluid stream. It may be noted that high energy Venturi scrubbers (with initial liquid velocity lower than the gas velocity) and ejector Venturi scrubbers (initial liquid velocity higher than the gas velocity) have entirely different energy consumption, atomization and scrubbing characteristics. The present invention involves ejector type Venturi scrubbers. The kinetic energy of the high velocity liquid (with or without co-injected gas flow) is used to atomize the liquid and to pump the gas stream to be treated, generally through the scrubbing system and connecting ducts. The Venturi ejector is generally used with a downstream droplet eliminator, e.g. a gravity or inertial impact separator to remove scrubbing liquid from the gas stream. In particular a downstream mist eliminator can be used.

Optionally, a basic reagent is added, for example selected from the group consisting of: caustic, lime, limestone, hydrated lime, fly ash, magnesium oxide, soda ash, sodium bicarbonate, sodium carbonate, and mixtures thereof. This may be used for removal of acidic gases from the gas stream. Preferably, the reagent is added to a scrubbing liquid sprayed into the gas stream. Optionally the scrubbing liquid of a Venturi ejector comprises such reagent.

Preferably, an acidic reagent is added, more preferably selected from the group consisting of: acetic acid, boric acid, carbonic acid, citric acid, hydrochloric acid, hydrofluoric acid, nitric acid, oxalic acid, phosphoric acid, sulfuric acid, and mixtures thereof. This may be used for removal of basic gases from the gas stream, such as ammonia. Preferably, an acidic reagent is added in case of urea finishing off-gas. Preferably, sulfuric acid or nitric acid is added. Optionally, the scrubbing liquid of a Venturi stage comprises such acidic reagent, for example in the first (most upstream) Venturi stage, or in the downstream second Venturi stage.

Preferably, the acid or basic reagent is added to a scrubbing liquid sprayed into the gas stream, preferably downstream of a first Venturi stage and preferably also downstream of a second Venturi stage. Optionally acid or basic reagent is comprised in a scrubbing liquid of a Venturi ejector, for instance of a first or second or optional third Venturi stage. A scrubbing solution from an acid scrubbing step comprising ammonium salt is for example supplied to a holding tank and/or outside battery limits, in particular if the acid reagent is introduced into the gas stream downstream of the first Venturi stage.

Preferably, the method involves acid scrubbing and dust scrubbing of urea prilling off gas, preferably carried out on top of a preferably natural draft urea prilling tower, i.e. in an abatement system located at the top of a urea prilling tower.

In some embodiments, a stream comprising dissolved urea, such as a blowdown and/or purge stream, for example from the first Venturi stage and/or a quench stage wherein a scrubbing liquid with or without acidic or basic reagent is used, is supplied to a recycle vacuum evaporation section, to give water vapor and a concentrated urea solution. The recycle vacuum evaporation section is preferably separate from and additional to the evaporation section of a urea plant. The concentrated solution comprising urea is supplied to (a stream to) the urea finishing (e.g. granulation or prilling) and the urea is included in the solid urea product, e.g. granules or prills. The vapor is condensed and the condensate is preferably reintroduced in the described method as make up water, e.g. used for scrubbing the prilling off-gas with an aqueous solution comprising less than 5 wt. % urea, such as in the second Venturi stage. In case the process comprises acid scrubbing, the stream and concentrate may further comprise ammonium salts. A concentrate may also be supplied to a urea ammonium nitrate (UAN) plant or urea ammonium sulfate (UAS) plant and introduced into a UAN or UAS product stream. In some embodiments, the method comprises acidic scrubbing downstream of a first Venturi stage and/or first quench or scrubbing stage and the acidic scrubbing solution purge stream is disposed of separately from the scrubbing liquid used upstream of said acidic scrubbing. The scrubbing liquid used in a stage upstream of the acidic scrubbing comprising urea is subjected to such evaporation.

Preferably, the static (absolute) pressure at the exit of the Venturi ejector is nearly the same or slightly larger relative to the gas entrance of the Venturi ejector, e.g. at least 90% or at least 100% or at least 105% of the static pressure at the entrance. Preferably, the method comprises urea prilling in a natural draft urea tower and Venturi scrubbing with said Venturi ejector on top of said prilling tower, wherein the static pressure at the exit of at least one Venturi ejector is larger than at the entrance of the Venturi ejector. The preferred initial velocity and ratio of the scrubbing liquid can contribute to such advantageous static pressure at such exit of the Venturi ejector.

Preferably, at least some or all Venturi ejectors are arranged substantially horizontally, e.g. for substantially horizontal flow through the throat, for instance at an angle of less than 20° or less than 10° to horizontal. This allows for a compact design. Also possible is for instance that at least some or all of the Venturi ejectors have a vertical orientation. In that case, the Venturi ejectors are arranged for flow downward through the throat. This allows for a small pressure drop.

Optionally, the method comprises quenching the gas stream upstream of the first Venturi ejector, for example by a temperature decrease of at least 10° C. or at least 20° C. or to a gas temperature of less than 60° C., or of 50° C. or less, for instance by spraying an aqueous solution and evaporation of at least some water. Optionally, the quenching spray solution comprises at least 10 wt. %, or at least 20 wt. % or at least 30 wt. % dissolved material, e.g. urea. Optionally, the quench spray solution is at least in part obtained from recirculated Venturi scrubbing liquid, such as of a first Venturi stage. Optionally, the quench spray solution essentially consists of water. The quench solution is for example sprayed as fine mist and/or in cross flow or co-current flow.

Optionally, the gas is passed through a droplet removal device, such as a demister, between a first and second Venturi stage and/or after a second Venturi stage. Optionally the method comprises further downstream particle capture and/or gas treatment steps.

In some embodiments, the method is carried out at the top of a prilling tower, more preferably on top of a urea prilling tower. Preferably, at least the Venturi ejector is placed on or at the top of a prilling tower, in particular a urea prilling tower.

Optionally, the method comprises one or more scrubbing steps, comprising scrubbing the gas stream with a scrubbing liquid, e.g. by spraying. The method optionally comprises passing the gas stream through a third Venturi stage, e.g. a third Venturi ejector or a (high energy) Venturi scrubber. A third Venturi stage may for instance be positioned between the first and second Venturi ejector stage or downstream of the second Venturi ejector stage. An optional third Venturi stage may for instance operate with a scrubbing liquid comprising an acid reagent. In some embodiments, the draw is essentially provided by the Venturi ejectors. In the method, submicron particles are removed from the gas stream. Generally, particles larger than 1 µm are also removed. Soluble gases such as ammonia may also be removed.

The present invention also pertains to a gas stream treatment method comprising subsequently:

A. providing a gas stream, preferably comprising or essentially consisting off-gas from a urea finishing section, more preferably a urea prilling tower, preferably from a natural draft urea prilling tower, B. spraying an aqueous solution into the gas stream, preferably comprising 20 wt. % to 55 wt. % urea, optionally to cool by at least 10° C. or at least 20° C. or to a temperature of less than 50° C., preferably in cross-flow or co-current flow, C. passing the gas stream through a first ejector Venturi scrubber having a throat, wherein an aqueous scrubbing liquid preferably comprising 20 wt. % to 55 wt. % urea is sprayed into the gas stream in the direction of the throat, D. spraying an aqueous solution into the gas stream, preferably in co-current flow or cross-flow, preferably with a solution comprising 0 wt. % to 5 wt. % urea, and optionally comprising an acid, for example spraying with water, E. optionally passing the gas stream through a mist eliminator, F. passing the gas stream through a second ejector Venturi scrubber having a throat, wherein an aqueous scrubbing liquid preferably comprising 0 wt. % to 5 wt. % urea is sprayed into the gas stream in the direction of the throat, G. optionally spraying an aqueous solution into the gas stream, optionally comprising 0 wt. % to 5 wt. % urea, and/or comprising acid or base reagent, optionally in co-current flow, cross-flow or counter-current flow, and H. optionally passing the gas stream through particle removal device, such as a mist eliminator.

Usually, this preferred method comprises passing the gas stream through at least one mist eliminator after at least one Venturi stage. Preferably, this method is carried out in a system on top of a prilling tower (e.g. natural draft prilling tower), wherein the system comprises the Venturi stages. Preferably in spraying step D, second Venturi stage step F and/or step G, the solution and/or liquid comprises less than 2 wt. % urea, e.g. from 0 to less than 2 wt. % urea, such as 0-1.50 wt. % urea, and optionally consists of water. Introducing in steps D and G, optionally also in F, a liquid having relatively low urea concentration can promote condensation of water on submicron urea particles, resulting in particle growth and better removal in a particle capture device such as in step F and H. Preferably at least 5 g water/Nm$^3$ is evaporated in these steps D, F and/or G. Optionally, further steps are included, for example a mist elimination step upstream of step D, e.g. between steps C and D. Possibly one or more or all of said steps are carried out consecutively.

In step E and H, the mist eliminator is independently for instance a knitted wire mist eliminator, a (plain wire) mesh mist eliminator, and/or a vane mist eliminator, e.g. a corrugated plate, in particular a chevron shaped vane mist eliminator. A knitted wire mesh mist eliminator is especially suitable for droplets with 3-20 μm size, and typically works on interception. The separation efficiency for instance drops from 90% at 3 μm, to less than 20% for droplets smaller than 1 μm. Typical vane mist eliminators can remove 99% of particles of 10 μm and larger, especially at lower pressures. Vane mist eliminators are based on inertial impaction. Vane mist eliminators are more effective at higher velocities and greater droplets sizes than wire mesh mist eliminators. E.g. at higher gas velocities re-entrainment occurs for mesh mist eliminators.

Preferably, in step E and/or H, a vane type mist eliminator is used. For instance, by the upstream venturi ejector and spraying (preferably co-current spraying, especially for step E or both step E and H) upstream of the preferably vane type mist eliminator of step E, step H, or each of E and H, the particles grow to a droplet diameter allowing for good removal in step E and H, such as above 10 μm for in particular step H, The invention also pertains to a gas stream treatment method comprising these steps A to H, preferably with the described Venturi ejector wherein the scrubbing liquid has an initial velocity of at least 25 m/s and wherein the ratio of scrubbing liquid and gas flow is between 0.0005 and 0.0015 (m$^3$/h)/(m$^3$/h). Step A optionally comprises a step of urea prilling in a urea prilling tower, such as a forced draft, induced draft, and preferably natural draft urea prilling tower, typically comprising supplying air into said prilling tower and spraying urea solution (e.g. urea melt) from a distributor at the top of urea prilling tower, so as to solidify urea, to obtain solid urea-comprising prills, yielding an exhaust stream at the top part of said urea prilling tower as said gas stream of step A.

The invention generally also pertains to a gas stream treatment system comprising at least one Venturi ejector. The Venturi ejector may comprise a Venturi scrubber and upstream thereof a nozzle directed to the throat of the Venturi scrubber, further comprising a pump in fluid connection with said nozzle for pressurizing at least liquid supplied to said nozzle. Venturi ejectors with round throats as well as with rectangular throats can for example be used.

The system preferably comprises two Venturi ejector stages in series, preferably as described. Each Venturi ejector stage typically comprises a Venturi ejector comprising a converging part, a throat, and a diverging part, and a nozzle for spraying into said throat. Preferably, said Venturi stages are placed in series with each other with respect to the gas stream, with optionally one or more intermediate steps between them such as a spraying step and/or a mist elimination step. Preferably, the system is placed on top of a urea prilling tower, especially a natural draft urea prilling tower.

In a possible configuration, gas flows vertically down through the Venturi ejectors of the gas stream treatment sections, which is preferred if equipment size is not a constraint. Preferably, a gas stream treatment section comprising two Venturi ejectors in series, has a configuration wherein said Venturi ejectors are horizontally arranged, for a desirable small equipment size. Hence, a preferred gas stream treatment system, preferably for a method according to the invention, comprises two Venturi stages in series, wherein each of said two Venturi stages comprises a horizontally placed Venturi ejector comprising a converging part, a throat, and a diverging part, and a nozzle for spraying into said throat, wherein said Venturi stages are placed above each other. Spraying includes for example injecting a liquid jet which breaks up into a spray, such that a spray is provided into said throat. Preferably, the horizontally placed Venturi ejectors extend at least in part into a (e.g. vertical) scrubbing column. Preferably the Venturi ejectors extend at least in part, or entirely, under or above one of the mist eliminators and/or above at least one of the basins (reservoirs) for collecting liquids of such a scrubbing column. Preferably the two Venturi stages are connected by a scrubbing column. Preferably the system comprises two adjacent scrubbing columns integrated in a single casing, e.g. with a vertical wall dividing a casing (such as a vessel) into at least two scrubbing columns, wherein said scrubbing columns are configured for upward gas flow through such scrubbing column.

A preferred gas stream treatment system comprises two Venturi stages in series, with a spray section in between, wherein the spray section is more preferably for spraying a fine mist so as to provide for evaporation of sprayed liquid downstream a Venturi stage and upstream of a Venturi stage. Optionally, the system comprises a compressor in fluid communication with a dual fluid nozzle for providing compressed air. Preferably, the gas stream treatment system comprises a mist eliminator between the two Venturi stages, and preferably a second mist eliminator downstream of the second Venturi stage. Optionally, these features are combined with the mentioned system having horizontally placed Venturi ejectors.

Preferably each Venturi stage comprises a scrubbing liquid recirculation loop, in particular comprising a pump for pressurizing and recirculating scrubbing liquid to said nozzle. Preferably, the Venturi stages have separate recirculation loops. The separate recirculation loops allow for different chemical compositions of the scrubbing liquids of each stage. A recirculation loop may comprise a fluid communication line from a collection basin or sump where scrubbing liquid is collected to one or more spraying nozzles.

In a further preferred embodiment, which can be combined, the gas stream treatment system comprises a horizontally placed ejector Venturi scrubber comprising an open-ended converging tube or duct part, a throat, and an open ended diverging part and a spray nozzle positioned inside said converging part for spraying into said throat, and wherein the open end of said converging part is a gas inlet for the gas stream to be treated.

Preferably, the system comprises a sprayer between a first and a downstream second Venturi stage, for spraying an aqueous solution having a higher water concentration (i.e. lower concentration dissolved and particulate material) than the scrubbing liquid of the first Venturi stage.

Optionally, the gas stream treatment system has a fluid connection with a urea finishing section, in particular for off-gas of a urea granulation section of urea prilling tower. Optionally, the gas stream treatment system is located at the top of a urea prilling tower, such as on top of the tower.

The invention also pertains to a urea prilling tower, preferably a natural draft urea prilling tower, having a gas stream treatment system comprising a Venturi ejector at the top of the prilling tower, more preferably comprising two Venturi ejectors in series, and even more preferably a gas stream treatment system as described. Preferably, the gas stream treatment system comprises a section configured for dust scrubbing and a downstream section for acid scrubbing, wherein both sections are positioned at the top of a urea prilling tower. A gas treatment system at the top of a prilling tower is for example a gas treatment systems having an inlet at an elevation which is less than 5 m higher or less than 5 m lower than the outlet for off-gas of the prilling tower.

Optionally, the gas stream treatment system does not comprise a fan or blower. Preferably, the system does not comprise a fan or blower for producing a pressure drop of the gas stream.

Advantages of the method and system of the invention include a low pressure drop, good efficiency for removal of submicron particles, and compact design. Pressurizing a liquid such as the recirculating scrubbing liquid can be efficiently done using compact equipment, e.g. a pump. Atomizing the liquid with compressed air can also be efficiently done using compact equipment, e.g., a compressor. Further advantageous performance is achieved through the preferred inclusion of multiple stages employing progressively less concentrated aqueous solutions (e.g. lower urea concentration) to promote particulate growth by condensation on the surface of submicron particulate.

The invention also pertains to a method of modifying an existing plant, such as a urea finishing section and/or prilling tower, in particular a urea prilling tower, preferably a natural draft urea prilling tower, the method comprising adding a gas stream treatment system, preferably with two Venturi ejector stages in series, preferably a gas stream treatment system as described. The invention also pertains to a method of modifying an existing urea finishing section and/or prilling tower, in particular an existing urea prilling tower, preferably a natural draft urea prilling tower, the method comprising adding a gas stream treatment system comprising a Venturi ejector, preferably on top of the prilling tower. Preferably the gas stream treatment system comprises two Venturi stages in series. Preferably the system is a system as described and/or for the described methods. The invention also pertains to a method of modifying an existing urea finishing section having a Venturi ejector, comprising adding a Venturi ejector in series with said Venturi ejector.

Referring now to the drawings in general, the illustrations are for the purpose of describing a preferred embodiment of the invention and illustrating preferred features of the systems and methods, and are not intended to limit the invention.

FIG. 1 shows a non-limiting embodiment of the invention. The vessel 1 contains all of the components. The vessel 1 contains a first vertical column A and a second vertical column B connected essentially by horizontal venturi ejectors 3 and 6. The first column A has a gas inlet 18. Provided is an inlet zone 2 for the gas stream (e.g. at 90% to 110% ambient pressure) with spray nozzles 10. Spray nozzles 10 spray in cross-flow with the gas stream and downward. Sprays 10 may spray a solution obtained from reservoir 4. Spray nozzles 10 may provide for quenching of the gas stream. Spray nozzles 10 may provide for condensation of water on submicron particles and/or for scrubbing. Sprayed liquid with captured and dissolved particles is collected in reservoir 4 under spray nozzles 10. Further provided is Venturi ejector 3, e.g. a Venturi eductor 3. Venturi ejector 3 comprises a nozzle 11. The nozzle 11 sprays scrubbing liquid from the converging tube part into the throat 15 of the venturi ejector. The gas inlet opening 17 of the converging part of the ejector 3 is parallel to the opening of throat 15, these openings are vertical. Ejector 3 has a horizontal orientation. Dashed line 16 indicates that the gas inlet 18 of the gas inlet zone 2, the gas inlet of the ejector 3, and the gas outlet of Venturi ejector 3 have a centre on a common line, contributing to low pressure drop. The nozzle 11 is positioned inside the converging tube part, downstream of and spaced from the gas inlet 17 of the Venturi ejector 3. At the bottom of the gas inlet zone 2, a concentrated water reservoir 4 is provided. The reservoir 4 is e.g. for recirculating urea solution with a relatively high urea concentration. A purge stream can be withdrawn from the recirculating stream. The recirculation is to nozzles 10. Such a reservoir 4B is also provided in the second column B, e.g. for recirculating urea solution used as scrubbing liquid in nozzles 11. From the stream obtained from the outlet of ejector 3, droplets are removed, e.g. using a mist eliminator 5, e.g. a vane type mist eliminator. The liquid including captured urea is collected in reservoir 4B. The liquid in reservoir 4B, optionally together with liquid from reservoir 4A, e.g. if reservoir 4B and 4A are merged, is recirculated through a loop 19 to nozzles 11 of Venturi ejector 3 (with pressurizing) and optionally to spray nozzles 10. A purge stream is withdrawn from reservoir 4B and disposed of. The mist eliminator 5 can also comprises a mesh. Upstream of mist eliminator 5 spray nozzles 14 are provided.

These nozzles 14 spray optionally in co-current direction with the gas flow and optionally as fine mist, for instance with droplet size of less than 300 μm or less than 200 μm. They typically spray dilute water (e.g. low urea concentration), e.g. from reservoir 7. The spray nozzles 14 upstream of the mist eliminator 5 for instance spray an aqueous solution comprising less than 5 wt. % urea, such as essentially water. The compartment between Venturi ejector 3, or said spray nozzles 14, and second Venturi ejector 6, or mist eliminator 5, preferably provides sufficient residence time to allow for evaporation of e.g. at least 50 wt. % of the sprayed water and preferably for condensation on submicron particles.

Further provided is a second Venturi eductor 6 for spraying with dilute scrubbing liquid. The arrangement of the nozzle 12 is the same as for eductor 3, hence parallel to the gas flow. Also provided is a dilute water reservoir 7. Reservoir 7 can be provided with a recirculation loop comprising a pump to the spray nozzle 12 of eductor 6. Also provided is a mist eliminator 8, e.g. a vane type mist eliminator, for eliminating droplets e.g. as formed in the Venturi eductor. Mist eliminator 8 may comprise a mesh, chevron, or combinations of each. Mist eliminator 8 is shown with horizontal arrangement. Any arrangement, including vertical, of a mist eliminator is also possible.

Further provided is a scrubber 13 upstream of said mist eliminator 8, e.g. the mesh, for spraying liquid countercurrent into said gas flow. Cross-flow and co-current flow spraying are also possible for nozzle 13. The sprays can also be directed to the mist eliminator, for cleaning the mist eliminator 8. Reservoir 7 collects droplets from eductor 6 and from said scrubber 14. A purge stream from reservoir 7 can be disposed of e.g. by supplying to reservoir 4, in view of the evaporation of liquid from reservoir 4 in for instance spray 2. Acid or basic reagent is optionally used for scrubbing in the scrubber 13 downstream of Venturi eductor 6. In such a case, the purge stream from reservoir 7 is preferably not supplied to reservoir 4, but is disposed of separately.

More preferably, scrubber 13 uses acidic scrubbing solution, such as (dilute) nitric acid or sulfuric acid, for acidic scrubbing to remove ammonia. Also provided is an exit duct 9 for venting to the environment.

In operation, the particle-laden gases enter the inlet zone 2 where hot gases are initially cooled by evaporation of particle-concentrated water (e.g. an aqueous urea solution) from spray nozzles 10. The gases enter the first Venturi eductor 3 where the liquid motive force from spraying scrubbing liquid through the nozzle 11 propels the gases forward without requiring a pressure drop. In the first Venturi eductor 3, the gases are scrubbed with the scrubbing liquid. The gas stream typically is or becomes saturated with water, based on the partial water vapor pressure of the scrubbing liquid. Coarse particulate is collected and dissolved into the water and further concentrated in the concentrated water reservoir 4. A gas stream including droplets leaves the first Venturi eductor 3 and passes through a mist eliminator 5 including the spraying/scrubbing 14. The gas stream then enters the second Venturi eductor 6. Liquid from spray nozzles 12 and mist eliminator 5 and from the outlet of Venturi ejector 3 is collected in reservoir 4 at the bottom of the scrubbing column B. The water in reservoir 4 comprises e.g. at least 40 wt. % dissolved material and e.g. at least 80 wt. % of the total removed particulate matter (including scrubbed in spray 2). In the second Venturi eductor 6, optionally at least some water evaporates, optionally saturating the gases with more water. In each Venturi eductor, gas and liquid are mixed and typically particles are entrained in liquid droplets, and the droplets are removed from the gas stream downstream of the Venturi eductor. Gases continue through the second mist eliminator 8, including the spraying 13, and then exit the scrubber at exit duct 9. Liquid obtained from mist eliminator 8 is collected in reservoir 7 and may be recirculated to Venturi eductor 6. The liquid in reservoir 7 comprises e.g. less than 5 wt. % urea and e.g. less than 20 wt. % of total urea removed from the gas stream. The liquid 7 comprises ammonium salts if acidic scrubbing is used for nozzles 13, in such case the purge stream from reservoir 7 is not supplied to reservoir 4, but is disposed of separately.

The Venturi eductors (3, 6) are preferably mounted in a horizontal position thereby allowing a compact design minimizing height, and preferably above each other to reduce footprint.

The material of construction of the scrubber casing and the venturi eductors is optionally a light-weight material such as FRP (Fiber Reinforced Plastic).

The pressure drop over the scrubber is typically less than 250 Pa, but can be zero, depending on the inlet and outlet ducting pressure drop. In many instances, there will be a net pressure gain, for example of up to 500 Pa or even more, with the outlet pressure being higher than in the inlet pressure.

Figure 2:
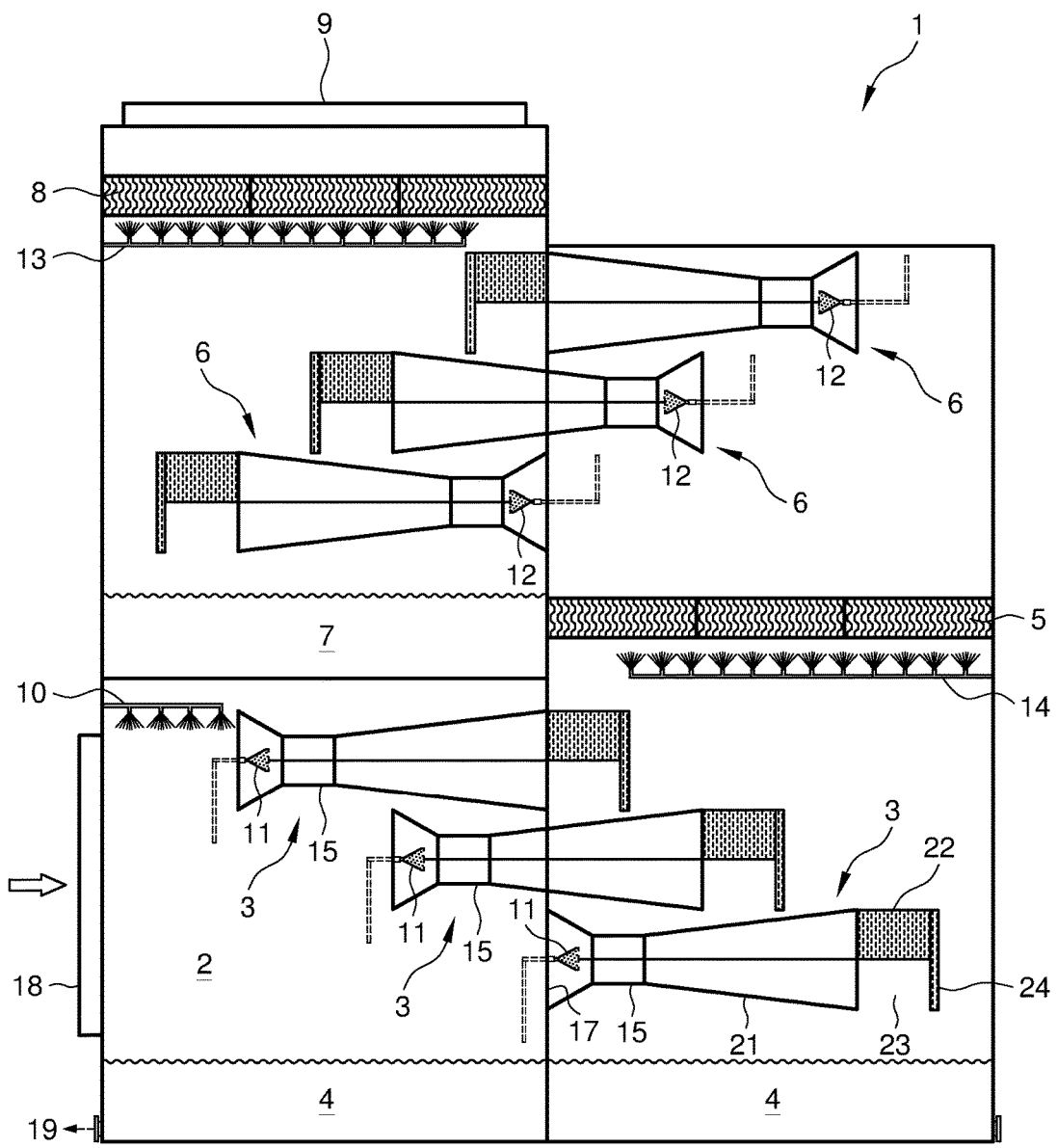
FIG. 2 depicts a block diagram of an embodiment of a system of the invention.

FIG. 2 shows an embodiment wherein the system comprises a plurality of parallel Venturi ejectors (3) and a second Venturi stage with a plurality of parallel Venturi ejectors (6). Herein the scrubbing column and the venturi ejectors are integrated in a single casing (1). Venturi ejector (3) extends horizontally under mist eliminator (5) and/or reservoir (7). The second Venturi ejector (6) stage extends horizontally above mist eliminator (5) and/or reservoir (7). A wall is provided between the two parts, at both sides in contact with process streams, separating the two halves, and only allowing for gas flow from one side to the other side through the Venturi ejectors (3,6). The diverging part 21 of the Venturi ejectors (3, 6) is provided at the upper side with an elbow 22 for gas/liquid separation having a bottom outlet 23 between the diverging part 21 end and a vertical separation wall 24.

Figure 3:
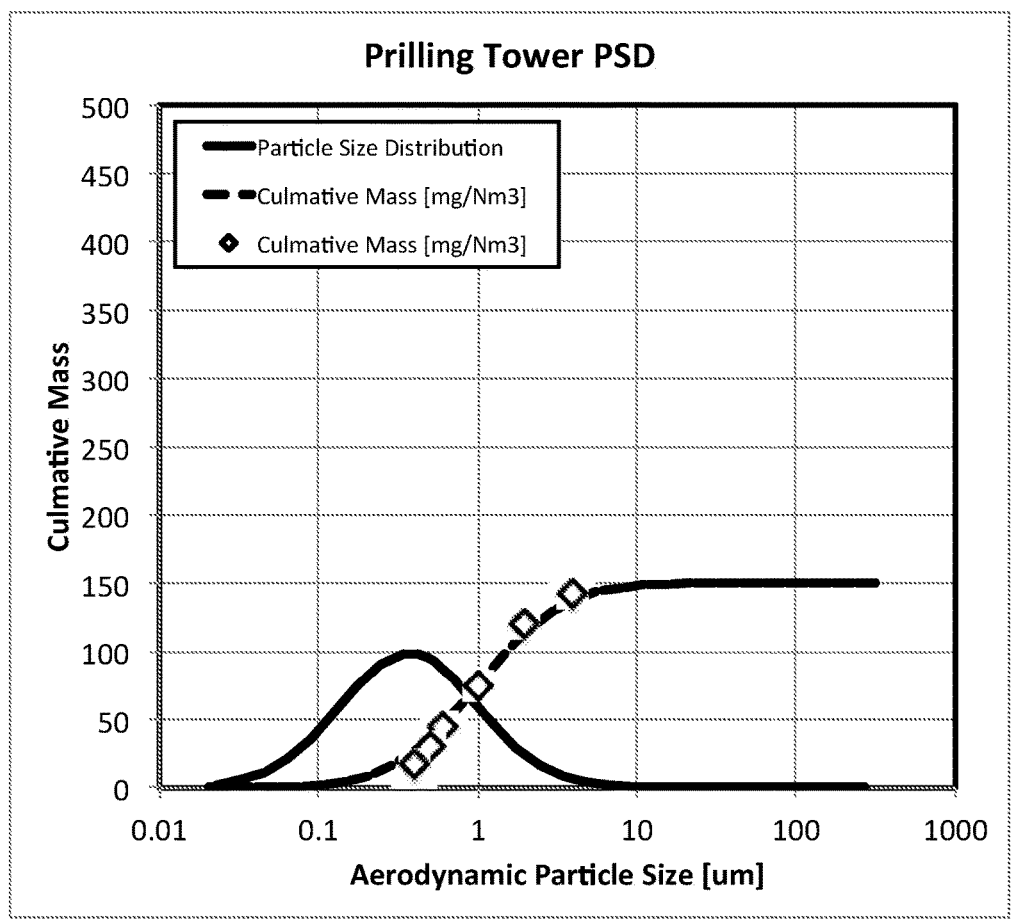
FIG. 3 shows a typical particle size distribution and cumulative mass for urea dust in off-gas from a prilling tower.

FIG. 3 shows a typical particle size distribution and cumulative mass for urea dust in off-gas from a prilling tower.

Figure 4:
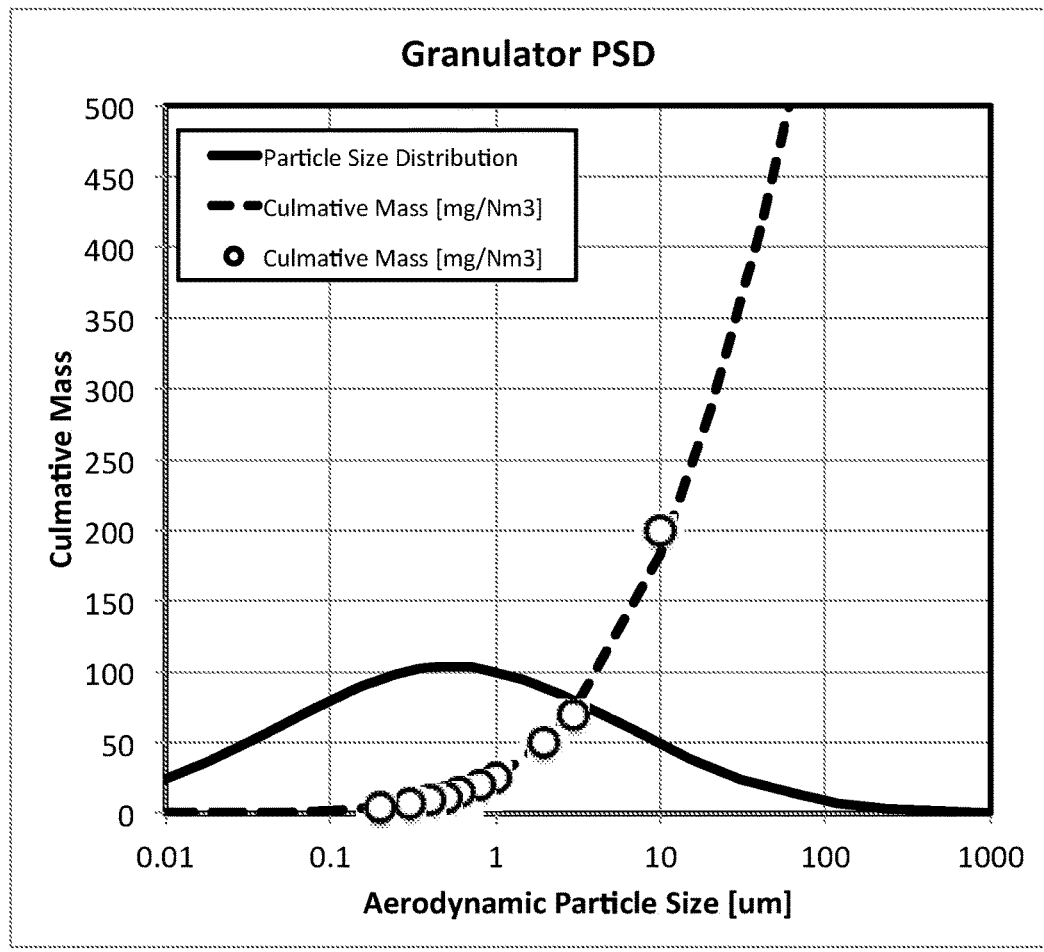
FIG. 4 shows a typical particle size distribution and cumulative mass for urea dust in off-gas from a urea granulator.

FIG. 4 shows a typical particle size distribution and cumulative mass for urea dust in off-gas from a urea granulator.

Example 1

The invention will now be further illustrated by an example, which does not limit the invention. As an example of a preferred embodiment, a prilling tower is proposed that has a urea-laden airflow that needs to be scrubbed. The temperature of the air leaving the prilling tower is 80° C., the molar fraction of water vapor is 2%, and the concentration of urea dust is 25 µg/g of gas flow. A Venturi eductor (ejector) spray is provided which will cool the air by evaporation until the airflow is saturated and water no longer evaporates. Using thermodynamic calculations in combination with steam tables, it is determined that this will occur at a final gas temperature of 33° C. with a water vapor molar fraction of 2.5% when using pure water. For this proposed project the amount of water evaporated is calculated to be 0.03 kg/Nm$^3$ of gas flow. However, in practice, the Venturi eductor spray will be recycled until the urea concentration approaches 45% wt. At this urea concentration, the vapor pressure of water is proportionally less. Using Raoult's law, the above calculations are repeated to find that the new saturated gas temperature is 37° C. with a water vapor molar fraction of 2.2%. Even though the saturated temperature is 4° C. higher, the molar fraction of water in the gas state is more than 10% less. Only 0.02 kg of water per Nm$^3$ of gas flow is predicted to evaporate, for the proposed project. Downstream of the concentrated Venturi eductor spray, when the gases are exposed to dilute water (e.g. aqueous urea solution having a lower urea concentration, such as essentially no urea), the saturated conditions will match the first case, enabling an additional 0.01 kg/Nm$^3$ of evaporation. By using a second dilute water spray that is preferably at least 0.2 seconds, or preferably 0.3 seconds, upstream of the dilute Venturi eductor (second Venturi stage), submicron particulate growth is promoted. This improves particle capture in for example a Venturi eductor. The dilute water spray is for example implemented as spray in a mist eliminator downstream of first Venturi stage and upstream of a second Venturi stage, allowing for condensation on submicron particles. A quench spray upstream of a first Venturi stage may promote initial condensation on submicron particles.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims and specification, the word "comprising" does not exclude other elements or steps, and the indefinite article "a" or "an" does not exclude a plurality. Terms such as "usually", "generally", "typically", "in particular", "can", "may" and "suitably" indicate non-essential features which may be omitted in some embodiments and can be combined with preferred features. The mere fact that certain features of the invention are recited in mutually different dependent claims does not indicate that a combination of these features cannot be used to advantage. Features of the methods can be combined with features of the system and features of the embodiments can be combined with features illustrated in the drawings. The preferred methods can for example be carried out in preferred systems and apparatuses.

The invention claimed is:

1. A method for removing submicron particles from a gas stream containing submicron particles said stream being off-gas from urea finishing, the method comprising: contacting the gas stream in a Venturi ejector with an injected high velocity scrubbing liquid to provide a pumping action, wherein the scrubbing liquid has an initial velocity of at least 25 m/s and wherein the ratio of scrubbing liquid and gas flow is between 0.0005 and 0.0015 $(m^3/h)/(m^3/h)$,
whereby the method comprises treatment in two Venturi stages in series, wherein each of said two Venturi stages comprises a horizontally placed Venturi ejector, wherein said Venturi stages are placed above each other, and whereby the two Venturi stages are connected by a scrubbing column.

2. The method of claim 1, wherein the gas stream is the off-gas from a urea granulator.

3. The method of claim 1 wherein the gas stream is the off-gas from a urea prilling tower.

4. The method of claim 3 wherein the residence time between the first and the downstream second Venturi ejector is at least 0.4 s.

5. The method of claim 4 wherein the residence time between the first and the downstream second Venturi ejector is more than 0.8 s.

6. The method of claim 1, wherein the gas stream contains a concentration of submicron particles greater than 20 $mg/Nm^3$.

7. The method of claim 1 wherein the Venturi ejector comprises a nozzle positioned for spraying scrubbing liquid in a direction parallel with the gas flow through the gas inlet of the Venturi ejector.

8. The method of claim 1 wherein a basic reagent is added selected from the group consisting of: caustic, lime, limestone, hydrated lime, fly ash, magnesium oxide, soda ash, sodium bicarbonate, sodium carbonate, and mixtures thereof.

9. The method of claim 1 wherein an acidic reagent is added selected from the group consisting of: acetic acid, boric acid, carbonic acid, citric acid, hydrochloric acid, hydrofluoric acid, nitric acid, oxalic acid, phosphoric acid, sulfuric acid, and mixtures thereof.

10. The method of claim 9, wherein the method comprises acid scrubbing and dust scrubbing, both carried out at the top of a natural draft urea prilling tower.

11. The method of claim 1, further comprising the step of urea prilling in a natural draft urea tower and wherein said Venturi ejector is positioned at the top of said prilling tower, and wherein the static pressure at the exit of at least one Venturi ejector is larger than at the entrance of the Venturi ejector.

12. The method of claim 1, comprising subsequently:
A) providing a gas stream,
B) spraying an aqueous solution into the gas stream,
C) passing the gas stream through a first ejector Venturi scrubber having a throat, wherein an aqueous scrubbing liquid is sprayed into the gas stream in the direction of the throat,
D) spraying an aqueous solution into the gas stream, and
F) passing the gas stream through a second ejector Venturi scrubber having a throat, wherein an aqueous scrubbing liquid is sprayed into the gas stream in the direction of the throat.

13. A method for removing submicron particles from a gas stream, according to claim 12, comprising subsequently:
providing a gas stream comprising off-gas from a urea prilling tower,
spraying an aqueous solution comprising 20 wt. % to 55 wt. % urea into the gas stream,
passing the gas stream through a first ejector Venturi scrubber having a throat, wherein an aqueous scrubbing liquid comprising 20 wt. % to 55 wt. % urea is sprayed into the gas stream in the direction of the throat,
spraying an aqueous solution comprising 0 wt. % to 5 wt. % urea into and co-currently with the gas stream,
passing the gas stream through a mist eliminator,
passing the gas stream through a second ejector Venturi scrubber having a throat, wherein an aqueous scrubbing liquid comprising 0 wt. % to 5 wt. % urea is sprayed into the gas stream in the direction of the throat,
spraying an aqueous solution comprising 0 wt. % to 5 wt. % urea into the gas stream, and
passing the gas stream through a mist eliminator.

14. A gas stream treatment system, comprising two Venturi stages in series, wherein each of said Venturi stages comprises a horizontally placed Venturi ejector comprising a converging part, a throat, and a diverging tube part, and a nozzle for spraying into said throat, wherein said Venturi stages are placed above each other, and wherein each Venturi stage comprises a scrubbing liquid recirculation loop comprising a pump for pressurizing and recirculating scrubbing liquid to said nozzle, wherein the Venturi stages have separate recirculation loops, further comprising a sprayer between a first and a downstream second Venturi stage, for spraying an aqueous solution having a higher water concentration than the scrubbing liquid of the first Venturi stage.

15. A urea prilling tower having a gas stream treatment system at the top of the prilling tower, said gas stream treatment system comprising two Venturi stages in series, wherein each of said Venturi stages comprises a horizontally placed Venturi ejector comprising a converging part, a throat, and a diverging tube part, and a nozzle for spraying into said throat, wherein said Venturi stages are placed above each other, and wherein each Venturi stage comprises a scrubbing liquid recirculation loop comprising a pump for pressurizing and recirculating scrubbing liquid to said nozzle, wherein the Venturi stages have separate recirculation loops.

16. A natural draft urea prilling tower, having a gas stream treatment system at the top of the prilling tower, wherein the gas stream treatment system comprises at least two Venturi ejector scrubbers in series.

17. The natural draft urea prilling tower of claim 16, wherein the gas stream treatment section comprises two Venturi stages in series, wherein each of said Venturi stages comprises a horizontally placed Venturi ejector comprising a converging part, a throat, and a diverging tube part, and a nozzle for spraying into said throat, wherein said Venturi stages are placed above each other, and wherein each Venturi stage comprises a scrubbing liquid recirculation loop comprising a pump for pressurizing and recirculating scrubbing liquid to said nozzle, wherein the Venturi stages have separate recirculation loops.

18. A method of modifying an existing prilling tower, comprising installing a the gas stream treatment system comprising two Venturi stages in series, wherein each of said Venturi stages comprises a horizontally placed Venturi ejector comprising a converging part, a throat, and a diverging tube part, and a nozzle for spraying into said throat, wherein said Venturi stages are placed above each other, and wherein each Venturi stage comprises a scrubbing liquid recirculation loop comprising a pump for pressurizing and recirculating scrubbing liquid to said nozzle, wherein the Venturi stages have separate recirculation loops on top of the prilling tower.

19. The method of claim 18, wherein the existing prilling tower is a natural draft urea prilling tower.

* * * * *